United States Patent [19]

Seden et al.

[11] Patent Number: 5,036,971
[45] Date of Patent: Aug. 6, 1991

[54] MOULDING CONTACT LENSES

[75] Inventors: William E. Seden, Fareham; David W. J. Shepherd, Eastleigh; Peter Henderson, Southampton, all of England

[73] Assignee: CooperVision Optics, Ltd., South Hampton, England

[21] Appl. No.: 446,635

[22] Filed: Dec. 6, 1989

Related U.S. Application Data

[62] Division of Ser. No. 107,593, Nov. 4, 1987.

[30] Foreign Application Priority Data

Jan. 28, 1986 [GB] United Kingdom ............... 8601967
Jan. 27, 1987 [GB] United Kingdom PCT/GB87/00045

[51] Int. Cl.$^5$ .......................................... B65D 81/22
[52] U.S. Cl. .................................... 206/5.10; 53/431; 249/82; 264/2.4; 264/2.6; 425/808
[58] Field of Search ....................... 206/5, 5.1; 249/82; 264/2.2–2.4, 2.6, 238, 313; 425/808; 53/431

[56] References Cited

U.S. PATENT DOCUMENTS

| | | | |
|---|---|---|---|
| 2,836,942 | 6/1958 | Miskel | 53/425 |
| 3,211,811 | 10/1965 | Lanman | 264/23 |
| 3,268,068 | 8/1966 | Le Grand | 206/5 |
| 3,422,168 | 1/1969 | Bowser | 264/2.2 |
| 3,499,954 | 3/1970 | Trojan et al. | 264/511 |
| 3,555,611 | 1/1971 | Reiterman | 425/808 |
| 3,741,377 | 6/1973 | Krellen | 206/5.1 |
| 3,894,710 | 7/1975 | Sarofeen | 425/808 |
| 3,977,517 | 8/1976 | Kadlecik | 206/5.1 |
| 4,042,652 | 8/1977 | Feneberg | 264/2.6 |
| 4,113,224 | 9/1978 | Clark | 249/105 |
| 4,165,158 | 8/1979 | Travnicek | 351/160 |
| 4,182,723 | 1/1980 | Covington | 264/2.3 |
| 4,209,289 | 6/1980 | Newcomb et al. | 264/2.2 |
| 4,211,384 | 7/1980 | Bourset | 249/160 |
| 4,284,399 | 8/1981 | Newcomb et al. | 425/808 |
| 4,349,470 | 9/1982 | Battista | 425/808 |
| 4,390,482 | 6/1983 | Feurer | 425/808 |
| 4,392,569 | 7/1983 | Shoup | 206/5.1 |
| 4,416,814 | 11/1983 | Battista | 264/1.1 |
| 4,447,372 | 5/1984 | Kreuttner | 425/808 |
| 4,640,489 | 2/1987 | Larsen | 249/122 |
| 4,650,616 | 3/1987 | Wajs | 264/2.6 |
| 4,761,069 | 8/1988 | Truong et al. | 264/2.3 |
| 4,782,946 | 11/1988 | Pollak | 264/2.6 |

FOREIGN PATENT DOCUMENTS

| | | |
|---|---|---|
| 0003695 | 8/1979 | European Pat. Off. . |
| 0064247 | 11/1982 | European Pat. Off. . |
| 2202301 | 7/1973 | Fed. Rep. of Germany ....... 206/5.1 |
| 2839249 | 3/1979 | Fed. Rep. of Germany ....... 264/2.2 |
| 3229270 | 2/1984 | Fed. Rep. of Germany . |
| 0081513 | 8/1963 | France . |
| 2399043 | 2/1979 | France . |
| 2494571 | 5/1982 | France .................................... 206/5 |
| 2565160 | 12/1985 | France . |
| 0299458 | 8/1984 | Switzerland . |
| 0909573 | 10/1962 | United Kingdom . |
| 0916377 | 1/1963 | United Kingdom . |
| 0967148 | 8/1964 | United Kingdom . |
| 1317005 | 5/1973 | United Kingdom . |
| 2048758 | 12/1980 | United Kingdom . |

Primary Examiner—Jimmy G. Foster
Attorney, Agent, or Firm—Vorys, Sater, Seymour & Pease

[57] ABSTRACT

A polyolefin mould for casting contact lenses from a polymerizable monomer composition which shrinks on polymerization, said mould comprising: male (50) and female (51) mould halves at least one of which has a flexible diaphragm portion (53, 54) which is shaped to provide a surface corresponding to a lenticular surface, said mould halves (50, 51), when closed together, cooperating to define a mould cavity (52) for receiving a volume of said monomer composition, at least one of said mould halves (50, 51) having a shoulder portion (55, 56) surrounding said cavity and shaped to engage with said other mould half to define an edge moulding portion of said cavity: whereby in use said diaphragm (53, 54) is deflected into said cavity under forces exerted on said mould by said monomer composition when polymerized in said closed cavity (52), thereby compensating for the shrinkage occurring on polymerization and avoiding the formation of bubbles or voids in the resulting lenses. In addition, the invention includes a method of casting contact lenses using a mould of the above kind.

10 Claims, 4 Drawing Sheets

MOULDING CONTACT LENSES

This is a divisional of co-pending application Ser. No. 07/107,593 filed on Nov. 4, 1987.

BACKGROUND OF THE INVENTION

This invention relates to a method for manufacturing contact lenses which involves casting a polymerisable monomer composition within a mould formed by two plastic mould halves. In addition, the invention extends to a novel design of plastics moulds for casting lenses and a system of manufacturing a packaged lens using elements of the mould in which it has been formed.

A method of growing importance for the large-scale manufacture of contact lenses comprises casting lenses in closeable moulds formed from a pair of co-operating mould halves. One problem which as to be overcome when casting lenses from polymerisable monomers in a closed mould system is to provide some means for compensating for the shrinkage which inevitably occurs when the monomer composition polymerises. Typically monomer materials used in contact lens production undergo a volumetric shrinkage of between 10 and 20%. Failure to compensate for this shrinkage will result in unacceptably high wastage rates and/or poor quality products containing voids or bubbles.

Various methods have been proposed for overcoming the problem of shrinkage during casting of monomer compositions. These have included providing a reservoir of monomer material which it is hoped will flow into and fill the cavity formed on shrinkage, see, for example, U.K. Patent specification No. 2,006,091. The difficulty with this kind of solution however is that the monomer tends to gel more rapidly in the confined area through which it is intended that the excess monomer should flow to reach the mould cavity.

One commercially successful solution to the shrinkage problem is taught by T. H. Shepherd in U.K. Patent No. 1,575,694. According to the Sheperd invention, a flexible peripheral rim or lip is provided on one of the two mould halves (normally the male mould half). The mould halves are designed so that the of closure of the mould the flexible rim contacts the corresponding surface on the other mould half to define the periphery of the mould cavity. When shrinkage occurs during polymerisation of the monomers, the flexible rim or lip deforms (normally inwardly) so as to permit the two mould halves to approach each other slightly more closely than when in the initial closed position. This slight movement of the mould halves towards one another during the polymerisation stage provides sufficient reduction in volume to compensate for the shrinkage of the monomers on polymerisation.

In general, and for many polymeric materials, the Shepherd method is extremely effective and has been very successful commercially. There are, however, some disadvantages which primarily arise from the way in which the edge of the cast lenses are formed. Satisfactory moulding of the delicate flexible rim or lip portion of the Shepherd mould requires great care and, in use, as the two mould halves are brought together, the flexible rim is easily distorted. This can result in a poorly shaped edge which, in many instances, requires mechanical polishing to be ophthalmically acceptable. In high quality lens production, edge polishing is necessary unless a very high rejection rate can be tolerated. While polishing is possible with many hydrophilic materials in their dry state this involves not only additional processing steps but incurs the danger of lens damage and losses during the dry processing stage. Furthermore, some lens materials such as silicon rubbers and fluorocarbon polymers are not capable of being polished because they are not sufficiently hard.

In one of its aspects the present invention is concerned with an alternative approach to the problem of compensating for shrinkage without the need to provide a flexible rim or lip on one of the mould halves.

U.K. Patent Specification No. 2 048 758 discloses a polypropylene mould for contact lenses, in which male and female parts of the mould have circumferential mating surfaces in the form of a horizontal shoulder on each mould part. The shoulders are formed as an interference fit so as to seal closely together when the male part is weighted at a load of 2 to 3 pounds, with the objective of avoiding flash at the periphery of the finished lens. The use of mating shoulders in this manner requires the two parts of the mould to meet with great accuracy to avoid variation in lens thickness around the lens.

SUMMARY OF THE INVENTION

According to the present invention there is provided a method of casting contact lenses in a closable plastics mould which comprises introducing a measured quantity of a polymerisable monomer composition into a female mould half having a curved surface which defines the front surface of the moulded lens and closing the mould with a male mould half having a curved surface which defines the back surface of the lens and effecting polymerisation of the monomer composition, wherein the portion of the closed mould which defines the edge of the resultant lens comprises a non-flexible shoulder constituting the perimeter of the curved surface on one of said mould halves and being sealingly engageable with the other mould half, and wherein the curved surface of at least one of the mould halves is formed with a diaphragm portion, said diaphragm portion being sufficiently flexible to move towards the opposite surface of the other mould half under the forces exerted by the shrinking monomer during polymerisation and thus compensate for consequential volume shrinkage.

The invention also includes a polyolefin mould for casting contact lenses from a polymerisable monomer composition which shrinks on polymerisation, said mould comprising: male and female mould halves at least one of which has a diaphragm portion which is shaped to provide a surface corresponding to a lenticular surface, said mould halves, when closed together, cooperating to define a mould cavity for receiving a volume of said monomer composition, at least one of said mould halves having a shoulder portion surrounding said cavity and shaped to engage with said other mould half to define an edge moulding portion of said cavity; said diaphragm being sufficiently flexible to be deflected into said cavity under forces exerted on said mould by said monomer composition when polymerised in said closed cavity.

A major difference between the present invention and the Shepherd process mentioned above is that the shoulder portion of the mould which surrounds the curved or lenticular moulding surface is essentially non-yielding compared with the diaphragm portion and the necessary volumetric shrinkage is compensated by flexing of the diaphragm portion or portions of the mould. These diaphragm portions of the mould are constructed from relatively thin plastics materials which, coupled with the other dimensions, including the diameter of the mould halves, enable the central areas of the two halves to deflect to take up the shrinkage.

The shoulder portion or portions of the mould are designed so that when the mould halves are brought together, the cavity is sealed in a liquid-tight manner. Preferably, the shoulder portion or portions are so shaped that when the two mould halves are brought together, the contact between the shoulder portions is essentially a line contact. It is also preferred for the shoulder on the female mould half to be formed with a slight return. This ensures that the moulded lens remains in the female mould half when the mould is opened.

The mould halves are preferably significantly larger than the lens to be moulded. This has several advantages. For example, an annular gap may be provided between the mould halves above the mould cavity, this annular gap acts as a reservoir which ensures that the mould cavity is completely filled as the mould is closed. It also provides a chamber within which the moulded flash can be retained. After the mould is opened, the flash is preferably retained on the male mould and this is ensured by forming a roughened surface on the outer part of the male mould half in this region.

A further and more significant advantage of using large mould halves is that the moulded lens can be readily hydrated within the female mould half. After hydration, a package for the hydrated lens can be formed by sealing a tear-off cap or lid to the flange of the female mould half.

Further features and advantages of the present invention will become apparent from the following description and accompanying drawings in which:

FIG. 8b is a plan view of the mould shown in FIG. 8a.

DETAILED DESCRIPTION

Figure 1:
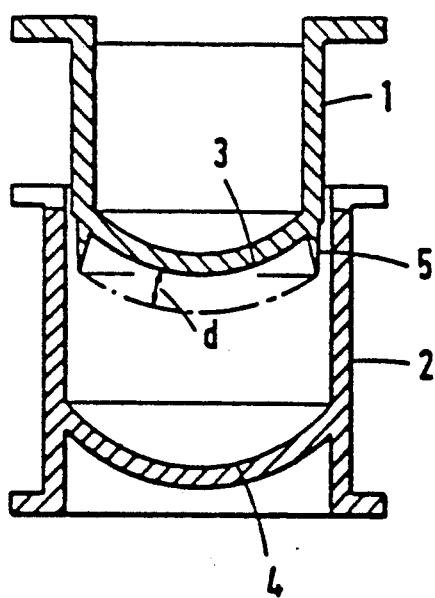
FIG. 1 is a sectional elevation of a Shepherd mould (in accordance with U.K. Patent No. 1,575,694) with the two mould halves about to be closed together.
Figure 2:
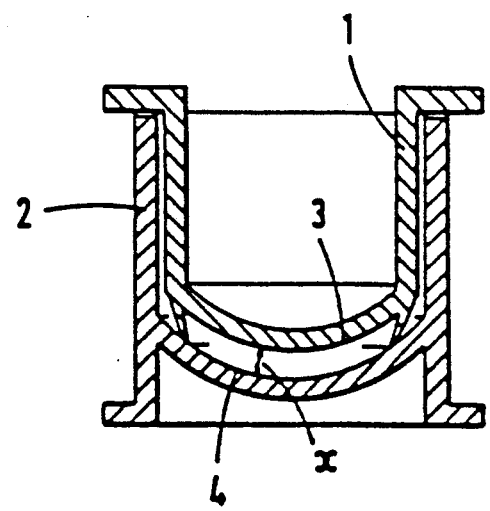
FIG. 2 is a view similar to FIG. 1 of a Shepherd mould but with the two mould halves in the fully closed position.

Referring to the drawings, FIGS. 1 and 2 show the male and female mould halves 1 and 2 respectively of a 'Shepherd' mould. Surfaces 3 and 4 of mould halves 1 and 2 are polished surfaces whose curvatures define the base curve and power curve, respectively, of the eventual cast lens. A flexible rim 5 is moulded integrally on the male mould half. On closing the mould, the rim 5 abuts the surface 4 and the height 'd' of the rim defines the initial depth and periphery of the mould cavity. As the monomer composition which is introduced into the mould cavity polymerises, shrinkage of the volume of the composition occurs. As a consequence, the rim 5 deforms inwardly as shown in FIG. 2 and the two mould halves move towards one another during polymerisation of the monomer composition so that they are separated by a final distance of 'x'. This represents the final thickness of the lens, if hard, or a proportion (usually about one half) if the lens is hydrophilic and subsequently hydrated.

Figure 7A:
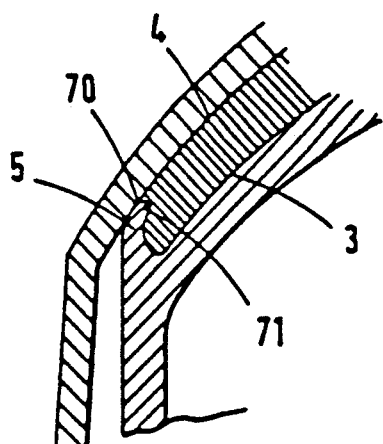
FIG. 7a is a scrap view on an enlarged scale of the edge of the lens mould in the Shepherd mould of FIGS. 1 and 2.

As can be seen in FIG. 2, the rim 5 commonly deforms inwardly, as a result of which, the lens is normally held onto the male mould half when the mould is opened. Occasionally, the rim deforms unevenly, peripherally of the lens, during polymerisation and a poor edge results. FIG. 7a shows a typical edge portion of a lens formed with a Shepherd mould, prior to polishing.

Figure 3:
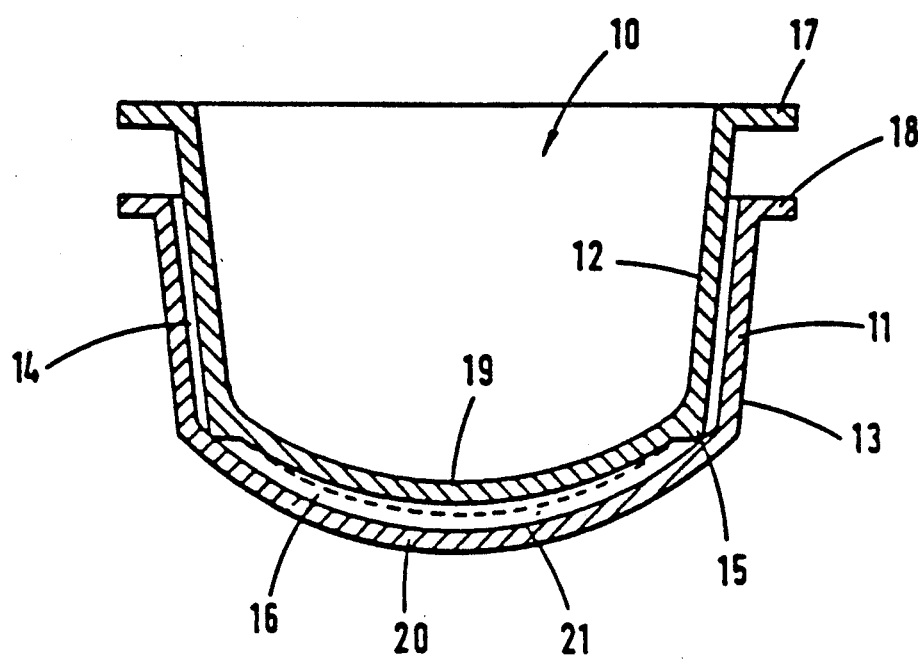
FIG. 3 is a view similar to FIG. 2 of a first embodiment of a mould in accordance with the invention.

FIG. 3 shows a first embodiment of a mould in accordance with the invention in the closed position. The mould consists of male and female mould halves 10 and 11, respectively. The body portions 12 and 13 of the mould halves have a slight downward taper so that the annular space 14 between them also tapers in the direction of the cavity. Closure of the mould is limited by the rim portion 15 of mould half 10 abutting against the surface 21 of the mould half 11, thereby defining a mould cavity 16. On closing the mould, with monomer composition filling the mould cavity, and applying a closing load to the mould, the flanges 17 and 18 may be deformed and welded together as described in our co-pending British patent application No. 86 06324 (Publication No. 2172839). The closing procedure with this embodiment may also be carried out as described in U.K. Specification No. 2172839.

Volumetric shrinkage is compensated by flexure of the portions 19 and/or 20, acting like a diaphragm under the suction or vacuum forces exerted by the shrinkage of the polymerising composition. Thus, the location of the inner surface of the portion 19 on the male mould half may be as indicated by dotted lines in FIG. 3 after completion of the polymerisation. The amount by which the diaphragm part of the mould is displaced depends on the nature of the polymerisable composition (including its volumetric shrinkage on polymerisation) and the volume of the lens mould cavity. Generally, the amount of displacement is about 10 to 40 microns, e.g. 10 to 25 microns.

Figure 6A:
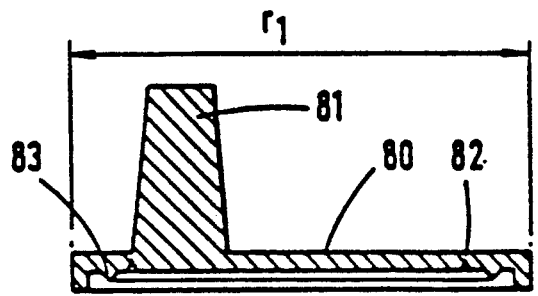
FIGS. 6a and 6b are views in section of the separated lid and female mould half of the package shown in FIG. 5.
Figure 5:
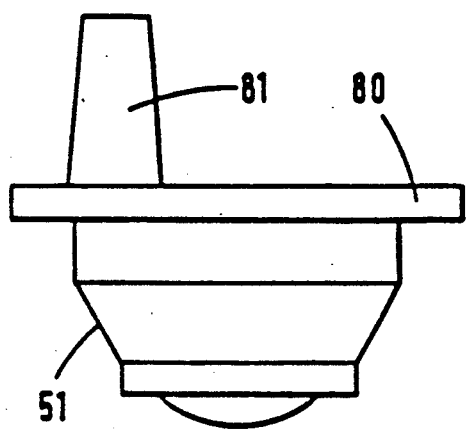
FIG. 5 is a side elevation of the mould shown in FIGS. 8a and 8b fitted with a tear-off lid to form a package.
Figure 6B:
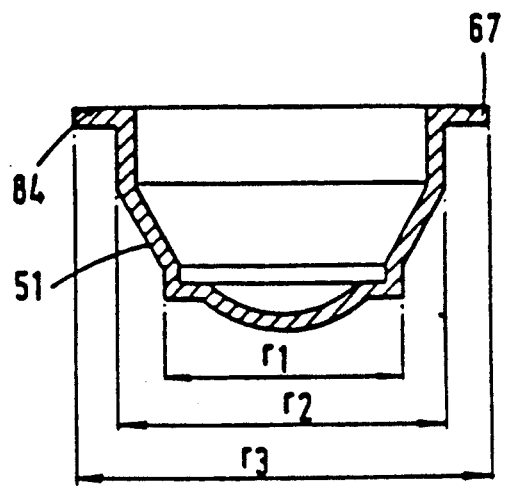

The moulds in accordance with the invention are themselves moulded by an injection moulding process using conventional moulding temperatures, pressures, speeds and dwell times. Each mould is normally a 'one-trip' mould, i.e. after casting a lens in the mould, the mould is discarded or used to form a package for the lens as described hereinafter in connection with FIGS. 5 and 6a and 6b.

It will be noted that, in comparison with the 'Shepherd' moulds, a solid shoulder portion 15 replaces the flexible rim 5. Greater rigidity in the shoulder region can be provided by thickening the mould material in this region or in the corresponding regions in the embodiments shown in FIGS. 4 and 8a and 8b. Also, as will be explained subsequently in connection with FIGS. 4 and 8a and 8b, by forming the mould halves with additional mating surfaces the whole mould is stiffened.

Figure 4:
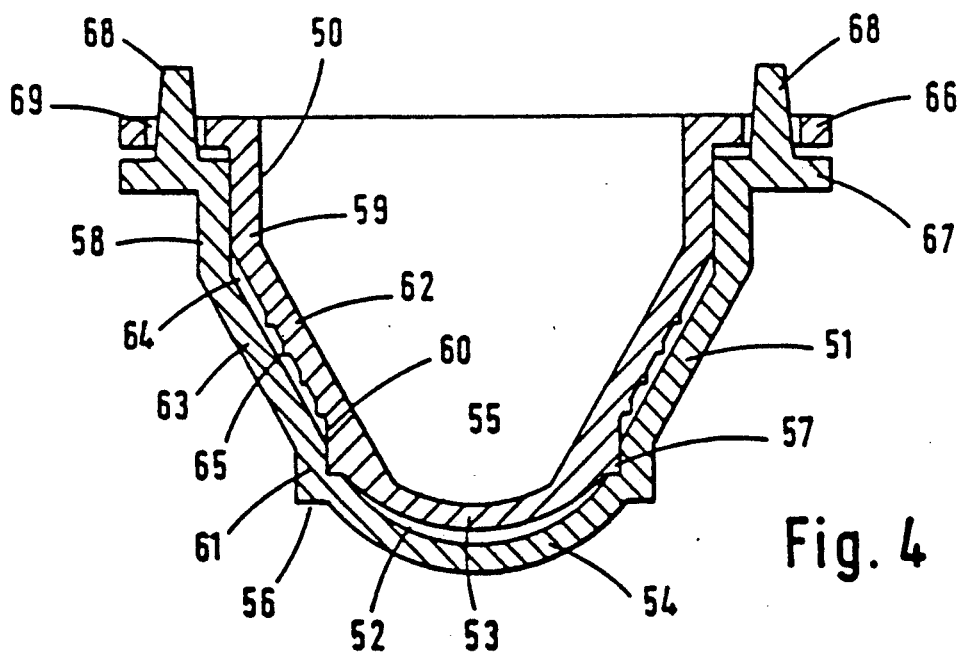
FIG. 4 is a sectional elevation of a second embodiment of a mould in accordance with the invention.

We find that when using a mould of the general form shown in FIGS. 3 and 4 and with an internal diameter of about 9 to mm, a wall thickness of 1 to 1.5 mm is satisfactory when using polypropylene moulds.

FIG. 4 shows a second embodiment of a mould produced in accordance with the invention and this embodiment (and that shown in FIGS. 8a and 8b) represent currently preferred forms. As can be seen, the mould is substantially larger in overall size than the mould shown in FIG. 3. The purpose of this is to enable the female mould half 51 to be used in a subsequent stage in the process as a receptacle for hydrating the moulded lens.

In common with the mould shown in FIG. 3, the mould of FIG. 4 comprises male and female mould halves 50 and 51 which when closed together, provide a mould cavity 52 for receiving a measured volume of polymerisable monomer. The cavity 52 is defined by two cooperating curved lens moulding portions 53 and 54 which are thin and flexible, e.g. from 0.6 to 1.4 mms thick, preferably 0.8 to 1.2 mms thick. The periphery of the moulding cavity 52 is defined by cooperating shoulder portions 55 and 56 whose cooperating surfaces are slightly inclined with respect to each other so that when the mould closes there is essentially line contact between the shoulders 55 and 56 while forming a liquid-tight seal. As will be described later with reference to FIGS. 7c, 7d and 7e, the inner edge 57 of the shoulder 56 is formed with a slight undercut or return which ensures that when the mould is opened the cured moulded lens remains in the female half of the mould.

Proper alignment of the mould during closure is ensured by providing axial aligning surfaces 58 and 59 on the upper portions of the male and female mould halves and also on the axial surfaces 60 and 61 of the shoulder portions 55 and 56. It will be appreciated that during closure of the mould, the surfaces 58 and 59 initially act to align the mould halves but as the mould continues to close, the surfaces 60 and 61 begin to cooperate to ensure accurate axial alignment of the mould halves during the final stages of bringing the mould halves together. The geometry of the two mould halves is arranged so that closure takes place along the generally radially extending cooperating surfaces of shoulders 55 and 56.

The outer diameter of the shoulder 55 is less than the inner diameter of the shoulder 56, but the two dimensions differ only slightly so that there is a sliding, aligning fit when the mould halves are closed together.

As can be clearly seen in FIG. 4, the wall portion 62 of the male mould is spaced from the corresponding wall portion 63 of the female mould half in the regions between the axially aligning surfaces. This provides an annular chamber 64 which acts as a reservoir and ensures that the mould cavity 52 remains completely filled during the mould closing operation. The outer surface of wall portion 62 is roughened, e.g. by forming a series of snatch rings 65 on its outer surface. This ensures that when the mould is opened, the connection between the moulded lens and the cured excess retained in the chamber 64 breaks cleanly at the point of cooperation between shoulders 55 and 56 and the excess cured material remains adhered to the roughened outer surface of wall portion 62.

Although the upper ends of the mould halves 50 and 51 are formed with flanges 66 and 67, similar to flanges 17 and 18 of the mould of FIG. 3, there is a functional difference in the construction of the flange portions. Whereas the mould halves in FIG. 3 are held together as described in the particular embodiment illustrated in our British Patent Application No. 86 06324 (Publication No. 2172839) by deforming the top flange, the need to deform the top flange may be avoided in the embodiment of FIG. 4. As can be seen in FIG. 4, flange 67 is formed with upwardly extending pegs 68 which are arranged to pass through corresponding apertures 69 in flange 66. Four pins or pegs may be uniformly distributed around the perimeter of the flange but the number can clearly be varied. When the mould is closed under a predetermined closing load applied to the top of flange 66, the mould halves are bonded together by deformation of the pegs 68. Preferably, this is achieved by means of a welding head which forms the projecting portion of the pegs 68 into a button which may be welded to the top portion of the flange 66 without significant distortion of the flange. It will be appreciated that this method (involving little or no flange distortion) avoids stresses which may be produced by deforming the top flange. Deformation of the top flange may be required if polymerisation temperatures induce relaxation of residual or applied stresses. Residual stresses are formed in both mould halves during injection moulding and applied stresses result from the application of the closing load. Relaxation of either of these two forms of stress may result in relative movement of shoulders 55 and 56, thus producing an unacceptable seal and lens edge form.

Figure 7B:
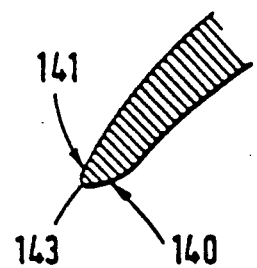
FIG. 7b is a similar view of an edge of a lens cast from a mould in accordance with the invention.

Referring to FIGS. 7a to 7e, these Figures illustrate the shape of moulded edges of lenses produced in accordance with this invention, compared with edges produced by the Shepherd process. FIG. 7a shows a typical edge profile moulded by the Shepherd process. As can be seen in FIG. 7a, after the lens has been cured, the flexible rim 5 has been turned inwardly thus gripping the cured lens onto the top of the male mould 1. Apart from presenting occasional problems in removing the moulded lens from the male mould half, this produces an edge having a sharp wafer edge 70 and an indented rim 71. Such an edge shape is generally unsatisfactory in causing discomfort to the wearer and would normally need to be polished to form an edge profile such as indicated in FIG. 7b. In order to remove the ragged edge of the lens shown in FIG. 7a, the lens surfaces 140 and 141, in the region of the edge, have been polished so as to form smoothed off surfaces 140 and 141 which terminate in a rounded edge profile 143 (see FIG. 7b). This involves an extra processing step which is desirable to avoid in large scale lens production, both because of its extra costs and because it is a source of possible contamination and introduction of inaccuracies.

Figure 7C:
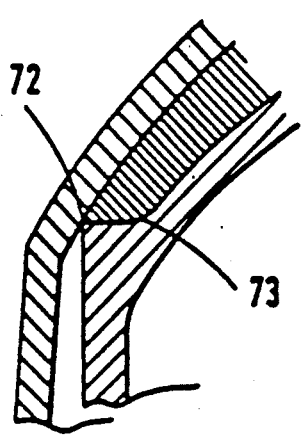
FIGS. 7c, 7d and 7e are scrap views, also on enlarged scales, of the edges of lenses in moulds in accordance with this invention.

Referring to FIG. 7c, this illustrates the kind of edge profile produced using a mould such as shown in FIG. 3. Although this lens has a relatively sharp perimeter 72 compared with that shown in FIG. 7b, it is nevertheless relatively comfortable to wear since the edge is generally uniform circumferentially of the lens in contrast to the edge shown in FIG. 7a. It must also be borne in mind that while the polishing operation will smooth out a ragged edge it is difficult to correct entirely a non-uniform moulded edge by polishing. The flat or slightly rounded portion of the edge 73 will contact the eye and such a surface is found to be generally comfortable. However, it is preferable to move the point at which the convex and concave surfaces merge away from the convex surface of the lens to avoid irritating the undersurface of the eyelid.

Figure 7D:
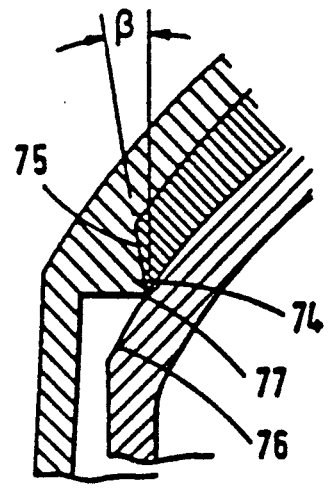

In addition, practical advantages arise from retention of the moulded lens within the female mould half and these improvements can be achieved by modification of the shape of the cooperating parts of the mould. Referring to FIG. 7d, this shows the situation where the shoulder 74 of the female mould half has been formed with a slight undercut 75. This undercut may be fairly slight, e.g. the angle B may be about 10° from the axis of the lens. Such an undercut will ensure that the lens after moulding remains in the female mould half and will be readily released on hydration without damage to the edge. In FIG. 7d, shoulder portion 74 cooperates with the lenticular surface 76 of the male mould and this results in the edge 77 being close to the concave surface of the lens.

Figure 8A:
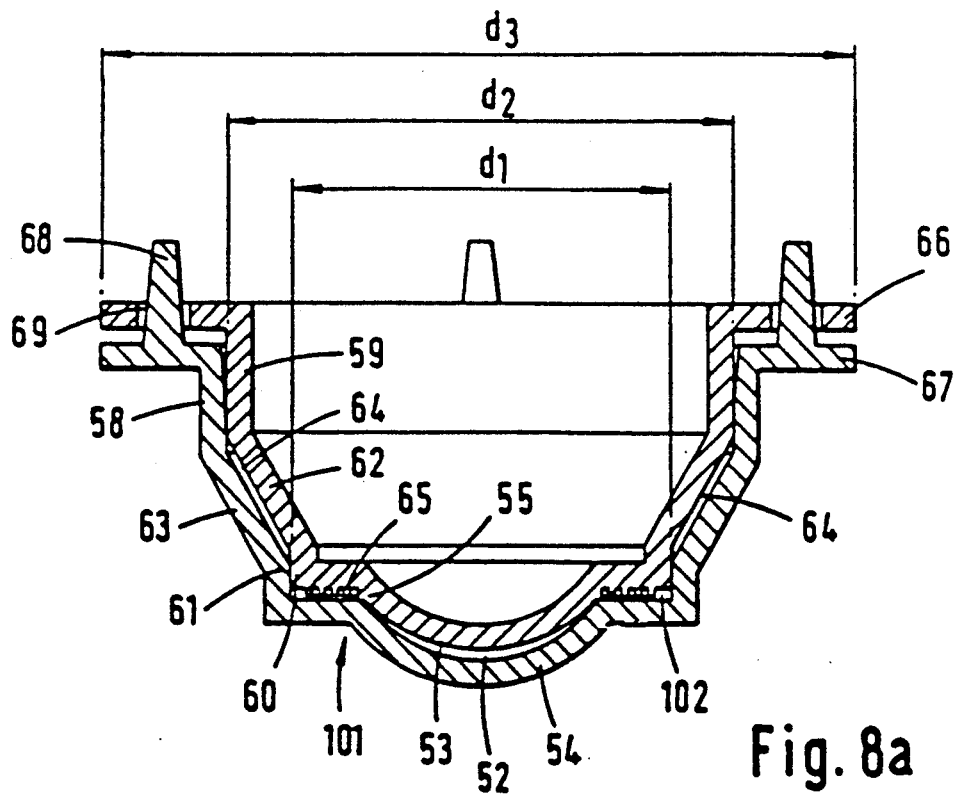
FIG. 8a is a view similar to that shown in FIG. 4 of a third embodiment of a mould in accordance with this invention.
Figure 8B:
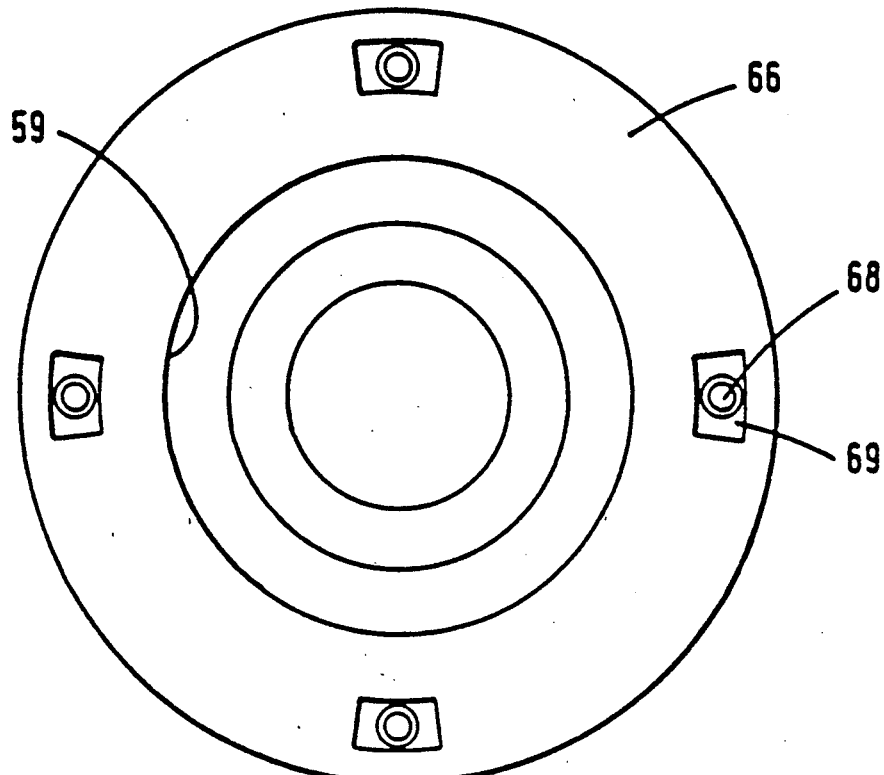

FIGS. 8a and 8b illustrate the presently most preferred embodiment in accordance with the invention. The mould shown in these Figures is similar to that shown in FIG. 4 and the same reference numerals are used for equivalent parts. The major difference is that a peripheral portion 101 housing a second reservoir 102 is located between the shoulders 55 and 56 and the snatch rings 65 are formed on the male mould within this reservoir portion. A clearance is provided between the wall portions 62 and 63 of the order of 0.5 mm, so as to form reservoir 64. Surfaces 60 and 61 are dimensioned to be a sliding fit and to provide a cooperating surface about 1 to 1.5 mms long. Similarly, surfaces 58 and 59 form cooperating sliding guide surfaces about 1.5 to 3 mms long, the upper 1.5 to 2 mms of the female mould being cut away to form a 3° to 5° outward lead taper about 1.5 to 2 mms long. The diameter of the lens cavity depends on the desired diameter of the lens; normally for soft contact lenses moulded as xerogels this is in the range of 8 to 10 mms. Typical dimensions for the dimensions $d^1$, $d^2$ and $d^3$ are respectively about 15, 20 and 30 mms. It will be appreciated that because of the sliding contact between surfaces 58 and 59 and between surfaces 60 and 61 and also as a result of the several angled surfaces formed in the mould hollows, the mould is stiffened overall, outside the region of the diaphragm portions 53 and 54. As can be seen from FIG. 8b, the flange 66 is formed with apertures 69 for receiving pegs 68. Apertures 69 provide sufficient clearance, particularly in a peripheral direction, to allow some tolerance when bringing the two mould halves together.

Figure 7E:
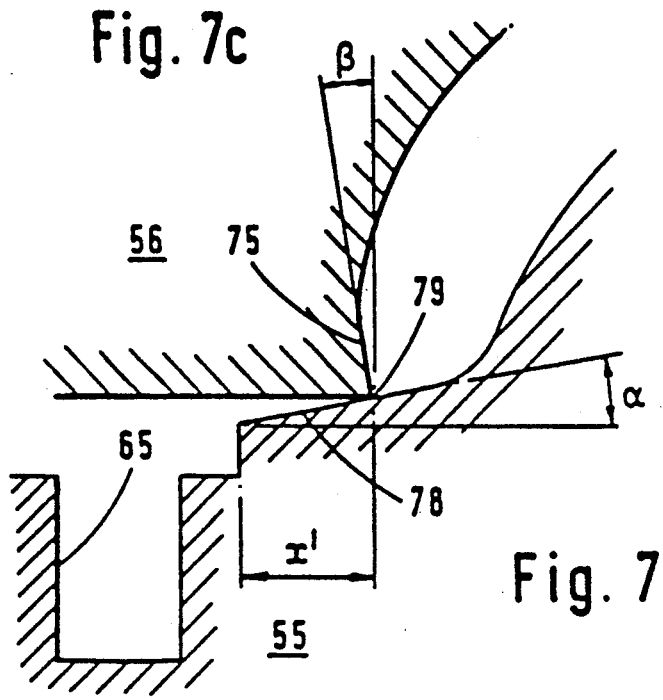

A preferred lens profile is shown in FIG. 7e, which illustrates the edge profile produced on moulding a lens using the mould shown in FIG. 8a, although similar considerations apply to the mould shown in FIG. 4. As can be seen from FIG. 7e, the edge portion is formed by cooperation between shoulders 55 and 56. Shoulder 55 has a undercut or return 75 (represented by angle $\beta$) similar to that shown in FIG. 7d, but because shoulder 56 has a top land 78, which is inclined to the plane at right angles to the axis of the lens, the concave and convex surfaces come together at an edge 79 which lies between the concave and convex surfaces of the lens. This produces a very comfortable moulded edge which does not require any polishing. The surface of the land 78 may be sloped by an angle (which is equivalent to angle $\alpha$) of about 4° to 10° to the radial plane and this is sufficient to produce line contact between the cooperating portions of the shoulders 55 and 56. The dimension $x^1$ of the cooperating portions of the shoulders 55 and 56 is of some importance and is preferably from about 0.1 to 0.2 mms.

Although in theory the diaphragm portions of the male and female mould halves should flex equally under the stresses exerted by the polymerising lens moulding composition; (provided that they are of similar thickness), it was found in practice using the particular injection moulding procedure adopted that substantially all the movement occured in the male mould diaphragm. The reason for this is not fully understood. However, the effect of differential injection pressures is considered to be at least a contributory factor and to cause the male mould diaphragm to be inherently slightly more flexible. It was found that with the particular moulding tools employed, optimum mould quality was achieved with a moulding pressure of 50 bar for the female mould and 30 bar for the male mould. Moulding temperature was substantially the same, the barrel temperature being about 210° C., and the bolster was cooled to about 40° C. Under these conditions of differential moulding pressure (significantly higher for the female), one would expect the higher moulding pressure to produce greater residual stresses and hence increased resistance to external loads. Whatever the precise reason for this difference, it is convenient in practice that movement is confined to the male mould diaphragm, since this makes it easier to predict the curvature of the surfaces of the cast lens.

Because, in accordance with the present invention, the shape of the edge is more predictable (since there is no longer any movement of the mould parts occurring at this point during casting), it is no longer necessary to polish the edge surface. Accordingly, in the practice of this invention for hydrogel lens production, after opening the moulds, the female mould halves containing the cast lenses can be immediately immersed in a hydrating bath. By virtue of retaining the lens within the female mould half, damage and contamination by handling is prevented. Surprisingly, it is found that hydration of the cast lenses while still retained in the female half will not result in distortions caused by uneven hydration provided that this is carried out in the proper manner.

The opening of the moulds and the hydration of the lenses can be mechanised. Thus, the moulds can be loaded into bowl feeders and orientated with their flanges uppermost and fed into tracks along which they are guided to a separating station where pneumatically driven knives sever the welds between the male and the female flanges, lift the male moulds and remove these by suction. The female mould halves containing the retained moulded lenses can then be picked up and placed by vacuum operated pick-up units into trays and from there loaded into a hydrating apparatus.

By arranging the moulds so that there is a substantial space for hydrating liquid, the lenses can be conveniently hydrated within the female mould halves without a significant risk of flushing the lenses out of the female mould cavities. It has been found that the lenses can normally be satisfactorily hydrated by several changes, (e.g. four to five) of hydrating liquid, depending on the polymer being cast. It may be desirable to gradually decrease the concentration of the saline hydrating liquid in successive aliquots of liquid since this appears to reduce the risk of stress cracks forming in the hydrated lenses.

Thus, in the operation of the process of the present invention the lenses are cast within their mould cavities, opened after the appropriate polymerisation and curing time has been completed and then immersed in a hydrating bath while still within their female mould halves. After recovery of the hydrated lenses from the diluted saline solution, a representative number can be checked for quality and adherence to specification. However, because of the predictability of the process, it is unnecessary to check every lens individually since it can be shown that they will all have the same optical properties within the tolerance limits of the manufacture of the original moulds. There is also a reduction in damage or contamination due to handling since the moulded lenses remain in the female mould half from the casting stage to final inspection.

Various other features can be adopted in the operation of the invention, including application of plasma arc or electron beam irradiation to one of the mould halves since this will tend to ensure that the lens will adhere to that mould half.

A further advantage of the mould shown in FIGS. 4 and i*a* and 8*b*, is that the female mould half can be adapted subsequently for forming a package for the final lens. Thus, referring to FIGS. 5 and 6*a* and 6*b*, a package can be formed utilising the female mould cavity 51 as a container closed with a suitably formed lid 80. It is important in packaging contact lenses, particularly hydrated contact lenses, that the package is hermetically sealed in order to prevent contamination from the outside or escape of liquid which could result in the lens drying and shrinking during storage or the storage solution concentrating and thus stinging the eye of the user when the lens is fitted. In the embodiment shown in FIG. 5, a tear-off lid 80 is provided which can be opened by pulling a tear peg or tag 81. The construction of the lid 80 is shown more clearly in FIG. 6. The lid 80 is formed from a sealable or heat-weldable material preferably from polypropylene or other plastic capable of withstanding sterilisation by autoclaving or irradiation. Polypropylene is an excellent choice of material since it can withstand auto-claving at temperatures in the region of 120° C. which is satisfactory for sterilising hydrated contact lenses. The lid 80 is formed with a circumferential notch 82 to enable a central circular portion of the lid to be removed by tearing on pulling the peg or tag 81.

Externally of the circular groove 82, the lid is formed with a circular rib 83. This rib is positioned so as to cooperate with a corresponding circular groove 84 in of the flange 67 of the female mould half. The shape of the rib also serves to concentrate the energy of an ultrasonic welding tool applied to the lid 80 and to weld the lid to the flange in the region of the rib 83, e.g. at the corresponding circular groove 84. Ultrasonic welding is also preferred since it has the effect of simultaneously dispersing liquid from the contact areas and effecting localised and reliable welding of the cooperating parts. This is particularly convenient since it means that the female mould halves containing swollen, hydrated lenses immersed in isotonic saline solution can be passed directly from the hydrating station to a station where a lid is fitted to form the packaged lens. After packaging, the lens is conveniently sterilised by heating the entire package in an autoclave to a temperature in the region of 120° C., finally inspected and shipped to the user. Typical values for the dimensions $r^1$, $r^2$, $r^3$ and $r^4$ are about 17, 22, 30 and 32 mms. A convenient total depth for the female mould half is about 12 to 15 mms.

Although this packaging method is described in relation to the use of female mould half for moulding soft contact lenses, the system could be used with modification for packaging soft contact lenses produced by lathing and hydrating within a concave container.

The process of the present invention can be used to cast any hydrophilic or hydrophobic lens composition, including hard lenses, such as polymethylmethacrylate, hard gas-permeable, fluorocarbon and silicon rubber lenses and soft (hydrogel) lenses, including those based on HEMA and copolymers thereof. Typical lens-forming polyerms are those mentioned in U.S. Pat. Nos. 4,469,646; 4,121,896; 3,539,524; 3,699,089; 3,700,761; 3,822,089 and U.K. Patents Nos. 1285677; 1475605 and 2138831.

We claim:

1. A packaged lens which comprises a container having a generally cup-shaped body portion, formed from a propylene polymer and having a tear-off lid propylene polymer hermetically sealed to the rim of said body portion, the resulting sealed package containing a sterilized lens and an aqueous storage liquid, wherein the body portion is a female mould half in which the lens has been cast.

2. A packaged lens according to claim 1 wherein the lid is attached to the body portion by ultrasonic welding.

3. A packaged lens according to claim 1 wherein the lens is a hydrogel lens.

4. A packaged lens for a moulded lens which comprises: a female mould component having a cavity for the moulded lens in which cavity the lens has been moulded and a surface configuration around the cavity which permits a male mould to be removed from the female mould without causing removal of the lens; and aqueous storage liquid; and a removable lid which sealingly covers the cavity containing the lens and the solution.

5. A method of packaging moulded contact lenses comprising the steps of:
   moulding polyerisable contact lenses in a mould including male and female halves;
   removing the male mould half after the monomer has cured while maintaining the moulded lens in the female halve;
   hydrating the moulded lens with an aqueous medium while the cured moulded lens is retained in the female mould half; and,
   closing the top of the female mould with a removable sealing member, thereby forming a sealed package containing the moulded lens and the aqueous medium.

6. The method of claim 3 wherein the female mould half is provided with at least a surface configuration surrounding the moulded lens so that when the mould is opened the lens remains in the female mould half.

7. The method of claim 6 wherein the moulded material forming the lenses is hydrophilic.

8. The method of claim 7 wherein the closing step is accomplished by using a removable cap.

9. The method of claim 8 which includes the further step of sterilizing the lens by heat treatment or irradiation while contained, in situ, in the package.

10. The method of claim 9 wherein the closing step is performed by ultrasonically welding the sealing member to the female mould so as to form a hermetic seal.

* * * * *